(12) United States Patent
Whitney

(10) Patent No.: US 8,838,464 B1
(45) Date of Patent: Sep. 16, 2014

(54) PRESCRIPTION MEDICATION MONITORING SYSTEM

(76) Inventor: Cecile Whitney, Newport Beach, CA (US)

( * ) Notice: Subject to any disclaimer, the term of this patent is extended or adjusted under 35 U.S.C. 154(b) by 1310 days.

(21) Appl. No.: 12/248,152

(22) Filed: Oct. 9, 2008

Related U.S. Application Data

(60) Provisional application No. 60/992,550, filed on Dec. 5, 2007.

(51) Int. Cl.
*A61B 5/00* (2006.01)
*G06F 19/00* (2011.01)

(52) U.S. Cl.
USPC .............................................. 705/3

(58) Field of Classification Search
CPC ....... G06Q 50/24; G06Q 50/22; G06F 19/323
USPC .......................................... 705/2, 3
See application file for complete search history.

(56) References Cited

U.S. PATENT DOCUMENTS

| | | | | |
|---|---|---|---|---|
| 4,766,542 A | * | 8/1988 | Pilarczyk | 705/3 |
| 4,916,296 A | * | 4/1990 | Streck | 235/454 |
| 4,976,351 A | * | 12/1990 | Mangini et al. | 206/232 |
| 6,019,284 A | * | 2/2000 | Freeman et al. | 235/380 |
| 2002/0032582 A1 | * | 3/2002 | Feeney et al. | 705/2 |
| 2002/0169635 A1 | * | 11/2002 | Shillingburg | 705/2 |
| 2003/0187690 A1 | * | 10/2003 | Miller et al. | 705/2 |
| 2003/0236681 A1 | * | 12/2003 | Ninomiya et al. | 705/2 |
| 2004/0232219 A1 | * | 11/2004 | Fowler | 235/380 |
| 2006/0094466 A1 | * | 5/2006 | Tran | 455/558 |
| 2006/0173718 A1 | * | 8/2006 | Murphy | 705/2 |
| 2008/0126135 A1 | * | 5/2008 | Woo | 705/3 |

* cited by examiner

*Primary Examiner* — John Pauls
*Assistant Examiner* — Trang Nguyen
(74) *Attorney, Agent, or Firm* — Kenneth L Tolar

(57) ABSTRACT

A prescription medication monitoring system includes a card having a microprocessor and an RFID chip embedded therein. The chip and microprocessor are electrically connected to a text display and multi-digit display on the front surface of the card. The card operates in conjunction with a base terminal located at a participating pharmacy. The base terminal initially uploads a patient's prescription and personal information via a designated server. The terminal also scans the patient's finger to create a fingerprint image, and then records the uploaded information, including the scanned fingerprint image, onto the chip. Pertinent information relating to the prescription, such as medication name, dosage amount, dosage frequency and remaining authorized refills can be readily depicted on the displays. Each time the patient refills a prescription, the process is repeated and the pertinent prescription data, including any remaining authorized refills, is automatically updated and can be accessed via the text display.

10 Claims, 3 Drawing Sheets

PRESCRIPTION MEDICATION MONITORING SYSTEM

CROSS REFERENCE TO RELATED APPLICATIONS

This application is entitled to the benefit of provisional application No. 60/992,550 filed on Dec. 5, 2007, the specification of which is incorporated herein by reference.

BACKGROUND OF THE INVENTION

The present invention relates to a unique system of recording, displaying and monitoring the active prescriptions of a given patient.

DESCRIPTION OF THE PRIOR ART

A doctor or a nurse practitioner typically handwrites a prescription, which the patient presents at a select pharmacy. Because the pharmacist filling the prescription usually has limited access to the patient's personal information, serious errors often occur. For instance, the pharmacist may be unaware of a particular allergy that could be fatal if the patient takes the prescribed medication. Sometimes, the pharmacist simply misreads or improperly fills a prescription causing a patient to take a medication that was not prescribed. In addition, a person other than the patient may present the prescription in order to obtain a controlled substance that would otherwise be unavailable. Accordingly, there is currently a need for a prescription monitoring system that overcomes the above-enumerated disadvantages.

A review of the prior art reveals a myriad of medication monitoring systems. For example, U.S. published patent application no. 20060010007 filed on behalf of Denman et al. discloses a patient prescription processing and monitoring system that uses a smart card to store patient medical data and prescription information.

U.S. published patent application no. 20040232219 filed on behalf of Fowler discloses a medical treatment and prescription administration verification method. The method includes using an identification card (i.e., "smart card") for storing, adding, deleting and modifying patient medical information including a microprocessor that is accessible by a card reader. The reader may include a fingerprint scanner for verifying the authenticity of the card carrier.

U.S. Pat. No. 6,873,960 issued to Wood et al. discloses a method of reducing fraud in healthcare programs including issuing a smart card to a patient and loading various personal information onto the card. A healthcare provider can later verify the identity of the card carrier when filling prescriptions or providing any other healthcare service.

U.S. Pat. No. 6,421,650 issued to Goetz discloses a medication monitoring system and apparatus including a patient component on which a patient's medical data is stored. The patient component is a battery-powered unit having a display screen and associated control buttons. The device further includes a card reader for retrieving a multitude of patient data stored on a smart card.

U.S. Pat. No. 6,397,190 issued to Goetz discloses a medication monitoring system and apparatus similar to that described in patent no. '650 that is adapted to monitor veterinary medication.

The prior art devices enumerated above do not include means for readily depicting a list of prescriptions pertaining to a given patient or a means for readily displaying vital information such as the number of remaining prescription refills for each medication; furthermore, the conventional systems contain no precautionary means for alerting a patient or a pharmacist if any prescribed medication adversely interacts with other medications. The present invention overcomes the deficiencies of the prior art medication monitoring systems by providing a card having displays that can selectively depict the number of active prescriptions, and pertinent information relative to each active prescription such as the remaining number of refills as well as a description and dosage of the pertinent medication; the system further includes a means for alerting a patient if an active prescription medication could adversely interact with any other substances.

SUMMARY OF THE INVENTION

A prescription medication monitoring system includes a card having a microprocessor and an RFID chip embedded therein. The chip and microprocessor are electrically connected to a text display and a multi-digit display disposed on the front surface of the card. The card operates in conjunction with a base terminal located at a participating pharmacy. The base terminal initially uploads a patient's prescription and personal information via a designated server. The terminal also scans the patient's finger to create a fingerprint image, and then records the uploaded information, including the scanned fingerprint image, onto the chip. Pertinent information relating to the prescription, such as medication name, dosage amount, dosage frequency and remaining authorized refills can be readily depicted on the displays. Each time the patient refills a prescription, the process is repeated, and the pertinent prescription data, including any remaining authorized refills, is automatically updated and can be accessed via the text display.

It is therefore an object of the present invention to provide a system that automatically records and monitors prescriptions.

It is another object of the present invention to provide a system that overcomes the dangers and inconveniences associated with filling prescriptions.

Other objects, features, and advantages of the present invention will become readily apparent from the following detailed description of the preferred embodiment when considered with the attached drawings and the appended claims.

DESCRIPTION OF THE PREFERRED EMBODIMENT

Figure 1:
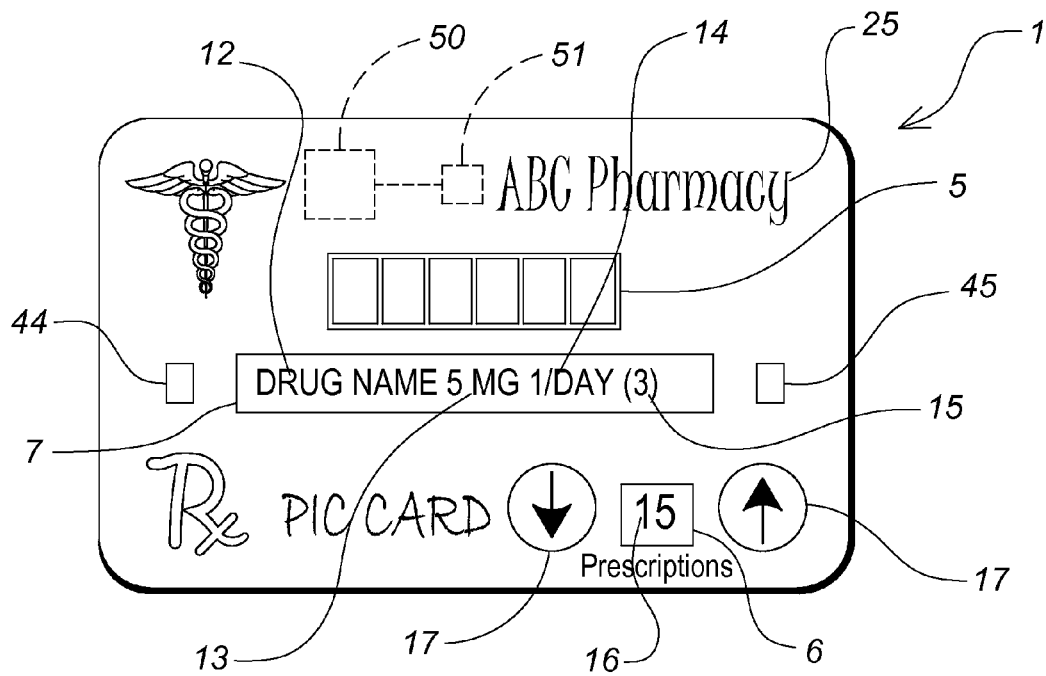
FIG. 1 is a front, plan view of the card according to a first embodiment of the present invention.
Figure 2:
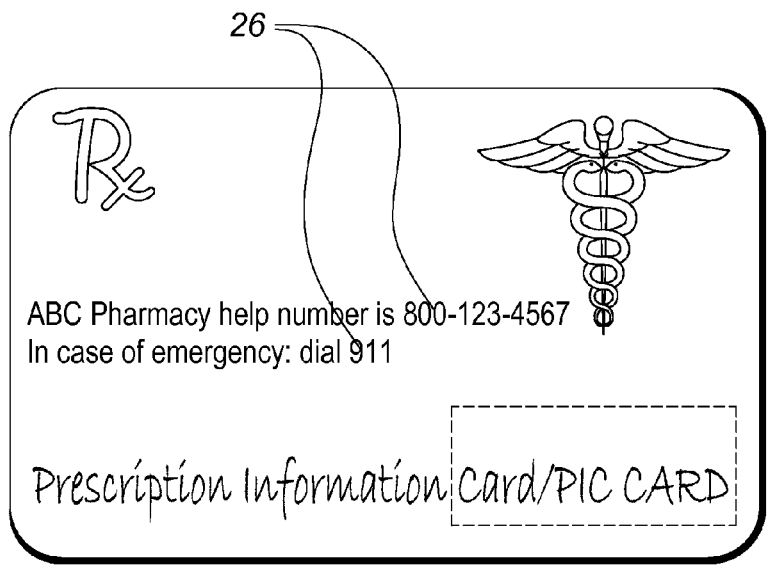
FIG. 2 is a rear, plan view of the card of FIG. 1.
Figure 3:
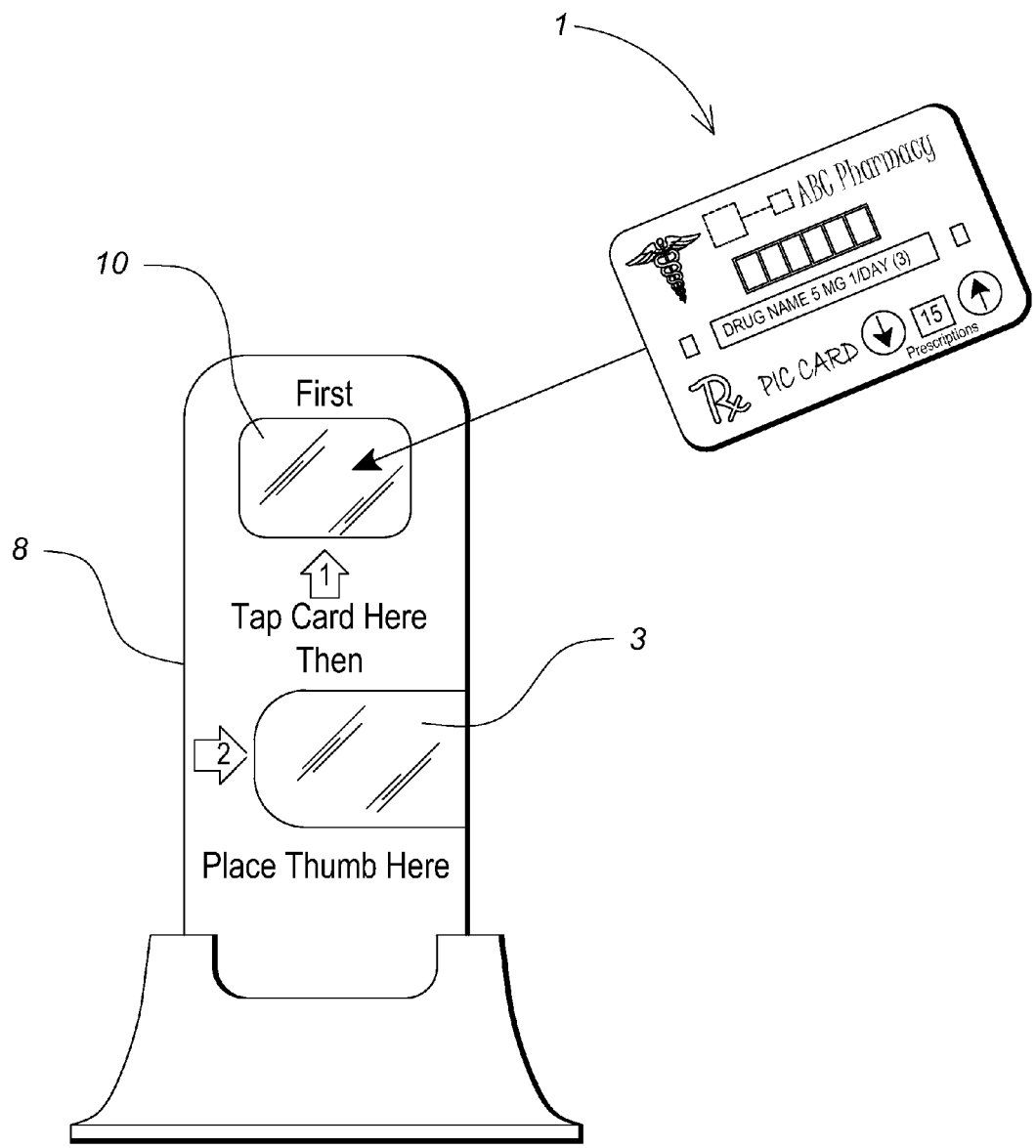
FIG. 3 depicts the associated base terminal.

A prescription medication monitoring system includes a card 1, similar to a conventional credit card, having a front surface and a rear surface. Preferably, the card is formed of two biodegradable layers with associated electronics positioned therebetween. The electronics include a low-profile, chip-on-board (COB) microprocessor assembly 50 in communication with an RFID chip 51. On the front surface of the card member is a solar cell array 5, a multi-digit display 6 and a text message display 7, all of which are electrically connected to the microprocessor.

The card operates in conjunction with a base terminal 8 located at a participating pharmacy. The base terminal is connected to a computer to establish communication with a designated server via the worldwide web. The terminal includes a fingerprint scanner 3 that initially scans a patient's fingerprint for later recording onto the card. When issuing a prescription, a healthcare provider initially uploads the patient's personal and prescription information to the designated server where it is accessible by the terminal. When the patient initially fills the prescription, he or she presents acceptable identification and places a finger on the fingerprint scanner to create a discrete fingerprint image associated with the patient. The terminal retrieves the patient's pertinent personal and prescription information from the designated server. The card is positioned adjacent a card reader 10 on the terminal, which emits an RF field to activate the RFID chip; the terminal then transfers all of the uploaded data, including all personal information, prescription details and the fingerprint image, onto the chip.

Virtually any data can be loaded onto the card's memory; an exemplary list of personal data is listed below:

---

Data that can be transferred to and be available on the card

---

Patient's name, address, phone numbers
Patient's personal information, i.e . . . , date of birth, etc.
Prescribed medicines, dosage, times per day, & remaining refills
Over the counter medicine(s) being taken
Applicable health conditions
Allergies & past surgeries
Prescribed glasses or contacts & the prescription, if available
Prescribed hearing aids & the type, if available
Dentist name, address, & phone number
Primary and secondary heath carriers, policy numbers, and contact phone numbers
Issuing doctor's name and contact phone number
Issuing pharmacy & contact numbers
Hospital choice with phone number and address
Emergency contact name(s) and phone number(s)
Living will or applicable medical directives
Can also be used for non-prescription health history

---

The microprocessor establishes communication between the chip and the card's displays so that the recorded data is readily visible by the carrier or pharmacist. Accordingly, when the card is exposed to ambient light, the text message display is activated on which the recipient's name appears for a predetermined period; immediately thereafter, data associated with the most recent prescription that was loaded onto the card is displayed. The display depicts the medication name 12, the dosage amount 13, the dosage frequency 14 and the remaining authorized refills 15. Simultaneously, the most recent prescription sequence number 16 is displayed on the multi-digit display to allow the carrier to immediately determine the total number of active prescriptions. A pair of scrolling switches 17 allow the carrier to sequentially display all of the above-described information related to any other active prescription loaded onto the card. Each time the carrier refills a prescription, the above-described process is repeated and the pertinent prescription data, including the remaining authorized refills, is updated.

The card also includes a pair of LED'S for alerting the card carrier of the refill status and the adverse interaction potential of each active prescribed medication. A first LED 44, adjacent an end of the text display, illuminates in a cautionary tone, i.e., yellow, if the selected, displayed medication is not authorized for any additional refills and that a new prescription must be obtained. A second, opposing LED 45 illuminates in a more urgent tone, i.e., red, if a select prescription medication may potentially interact with any other medications, whether prescribed or over-the-counter, or any other substances. Accordingly, the carrier can consult with the pharmacist to obtain more detailed information on the possible interaction(s). Furthermore, the card may be linked with financial institutions, such as banks or credit card companies, so that payment for the prescription is automatically finalized when the prescription is filled.

Figure 4:
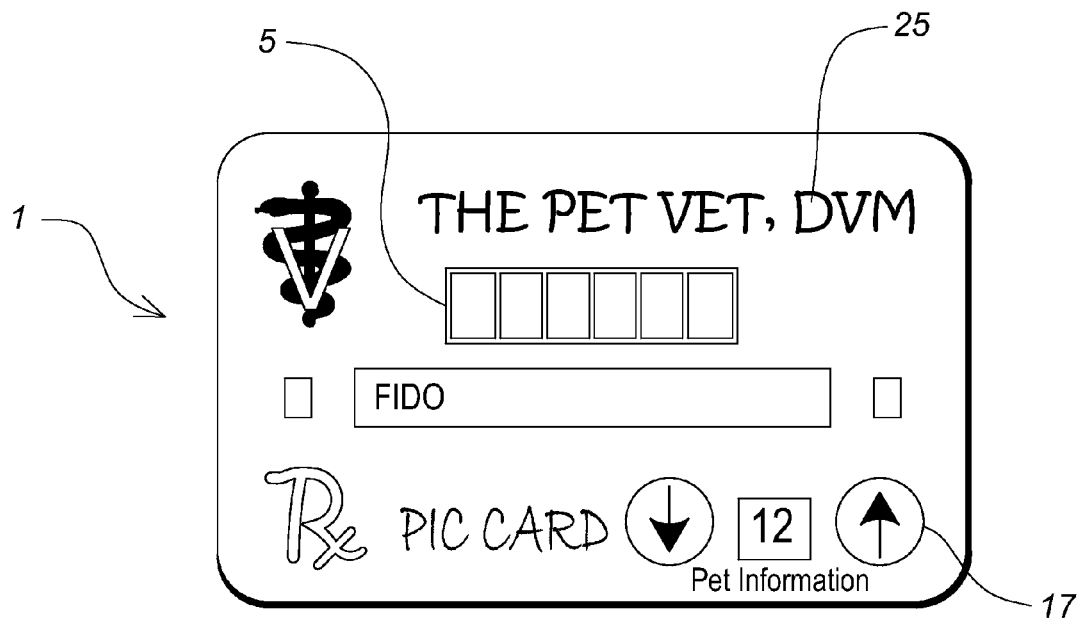
FIG. 4 is a front, plan view of the card according to a second embodiment of the present invention.
Figure 5:
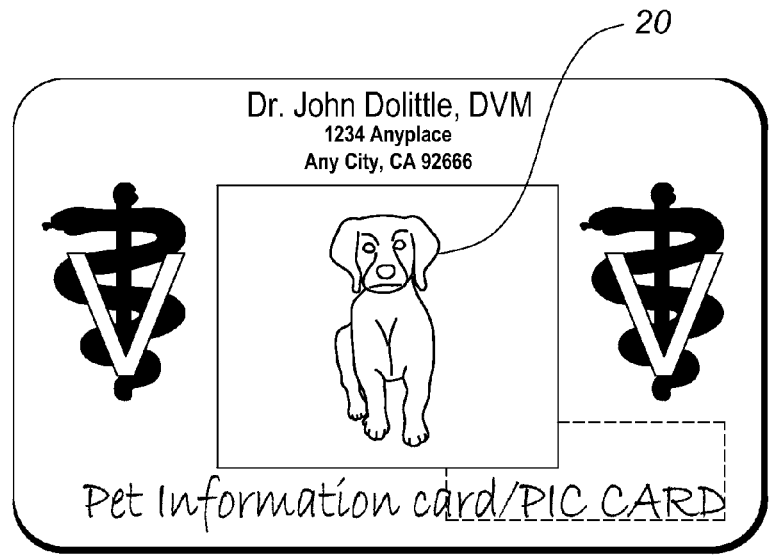
FIG. 5 is a rear, plan view of the card of FIG. 4.

Now referring to FIGS. 4 and 5, the above-described system can also be used to record and monitor a pet's medical data, including that related to prescribed medications. The card and base terminal are identical to that described above. Various data related to the pet's medical history can be loaded onto the card such as:

---

Owner's name
Owner's address
Home phone number
Cellular phone number
Pet's name
Breed and type of the pet/animal
Height & weight
Date of birth
Health history/surgeries/vaccinations
Veterinarian name, address, & phone number

---

The pet's photograph 20 may be digitally imprinted onto the rear surface of the card. Furthermore, any data associated with an identification chip imbedded within the animal can be loaded onto the card's RFID chip. Accordingly, the pet's owner can place the card in a purse or wallet thereby providing continuous access to the pet's medical history, even in emergency situations when such information would otherwise be unavailable. Either of the above-described cards can include advertising logos 25, emergency numbers 26 and other similar information imprinted onto either side of the card.

The above-described device is not limited to the exact details of construction and enumeration of parts provided herein. Furthermore, the size, shape and materials of construction of the various components can be varied.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

The invention claimed is:

1. A prescription medication monitoring system comprising:
    a card having a front surface and a rear surface, said card having a data-recordable chip embedded therein;
    a multi-digit display and a text message display on the front surface of the card;
    means for downloading onto said chip a patient's personal information and authorized prescription information, said prescription information including a description, a dosage amount, a dosage frequency and an authorized number of refills corresponding to each of a plurality of authorized prescription medications;
    means for depicting the prescription information for a select one of said authorized prescription medications on said text display;
    means for selectively displaying a prescription sequence number for a select one of said authorized prescription medications on said multi-digit display, said sequence number corresponding to an order in which said select one of said authorized prescription medications was loaded onto said chip relative to any other authorized prescription medications.

2. The prescription medication monitoring system according to claim 1 further comprising a solar cell array on the front surface of said card, said array electrically connected to said text display, said multi-digit display and said chip to provide electrical power thereto when said card is exposed to ambient light.

3. The prescription medication monitoring system according to claim 2 further comprising means for selectively depicting a patient's name on said text display for a predetermined duration.

4. The prescription medication monitoring system according to claim 3 further comprising means for allowing a carrier of said card to sequentially display the prescription information corresponding to all authorized prescription medications on said text display.

5. The prescription medication monitoring system according to claim 4 wherein said means for allowing a carrier of said card to sequentially display prescription information corresponding to all authorized prescription medications on said text display comprises a pair of scrolling switches that, when depressed, sequentially depict the prescription information for each of said authorized prescription medications.

6. The prescription medication monitoring system according to claim 5 further comprising a means for alerting a carrier of said card that a select authorized prescription medication has no remaining authorized refills.

7. The prescription medication monitoring system according to claim 6 further comprising means for alerting a carrier of said card that a select authorized prescription medication is potentially adversely interactive with another substance.

8. The prescription medication monitoring system according to claim 7 wherein said means for downloading onto said chip a patient's personal information and authorized prescription information comprises:

a base terminal in communication with a server having said patient data and said prescription information uploaded thereon, said terminal including a card reader in wireless communication with said chip for transferring said patient data thereto when said card is positioned adjacent to said card reader.

9. The prescription medication monitoring system according to claim 8 wherein said terminal further includes a fingerprint scanner that scans a patient's fingerprint and creates an image thereof for recording onto said chip and for subsequently verifying a patient's identity when said card is subsequently presented.

10. The prescription medication monitoring system according to claim 9 further comprising means for initially displaying prescription information and the prescription medication sequence number associated with a most recently downloaded prescription medication when said card is exposed to ambient light.

* * * * *